(12) United States Patent
Salako-Akande

(10) Patent No.: US 11,246,892 B1
(45) Date of Patent: Feb. 15, 2022

(54) METHOD AND COMPOSITION FOR AMELIORATING DRUG SEEKING BEHAVIOR

(71) Applicant: Ajibike Omosalewa Salako-Akande, Halethorpe, MD (US)

(72) Inventor: Ajibike Omosalewa Salako-Akande, Halethorpe, MD (US)

(*) Notice: Subject to any disclaimer, the term of this patent is extended or adjusted under 35 U.S.C. 154(b) by 149 days.

(21) Appl. No.: 16/708,843

(22) Filed: Dec. 10, 2019

Related U.S. Application Data

(60) Provisional application No. 62/777,529, filed on Dec. 10, 2018.

(51) Int. Cl.
| | | |
|---|---|---|
| A61K 31/00 | (2006.01) | |
| A61K 35/60 | (2006.01) | |
| A61P 25/30 | (2006.01) | |
| A61K 31/4415 | (2006.01) | |
| A61K 33/08 | (2006.01) | |
| A61K 33/10 | (2006.01) | |
| A61K 31/07 | (2006.01) | |
| A61K 31/375 | (2006.01) | |
| A61K 31/59 | (2006.01) | |
| A61K 31/355 | (2006.01) | |
| A61K 31/122 | (2006.01) | |
| A61K 31/51 | (2006.01) | |
| A61K 31/525 | (2006.01) | |
| A61K 31/455 | (2006.01) | |
| A61K 31/519 | (2006.01) | |
| A61K 31/4188 | (2006.01) | |
| A61K 31/197 | (2006.01) | |
| A61K 31/714 | (2006.01) | |
| A61K 33/06 | (2006.01) | |

(Continued)

(52) U.S. Cl.
CPC .............. *A61K 35/60* (2013.01); *A61K 31/01* (2013.01); *A61K 31/05* (2013.01); *A61K 31/07* (2013.01); *A61K 31/122* (2013.01); *A61K 31/197* (2013.01); *A61K 31/198* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/714* (2013.01); *A61K 33/00* (2013.01); *A61K 33/06* (2013.01); *A61K 33/08* (2013.01); *A61K 33/10* (2013.01); *A61K 33/18* (2013.01); *A61K 33/20* (2013.01); *A61K 33/24* (2013.01); *A61K 33/26* (2013.01); *A61K 33/30* (2013.01); *A61K 33/32* (2013.01); *A61K 33/34* (2013.01); *A61K 33/42* (2013.01); *A61P 25/30* (2018.01)

(58) Field of Classification Search
CPC .................................................... A61K 31/00
See application file for complete search history.

(56) References Cited

FOREIGN PATENT DOCUMENTS

JP 2011528321 A * 11/2011 ............. A61K 45/06

OTHER PUBLICATIONS

English machine translation of Blum et al., JP 2011-528321 A, 2011.*

* cited by examiner

*Primary Examiner* — Rosanne Kosson
(74) *Attorney, Agent, or Firm* — Whiteford, Taylor & Preston, LLP; Peter J. Davis

(57) ABSTRACT

A composition and method for ameliorating drug-seeking behavior in drug addicts who have stopped using the addicted-to drug and who have reestablished non-addict physiological chemical balance.

3 Claims, 5 Drawing Sheets

Phase of Experiment

T-test results of percent time spent in the aversive white CPP chamber for the baseline, amphetamine withdrawal period and post 8 weeks of either nutritional supplementation or normal rat chow

*$p<0.05$ compared to baseline
**$p<0.05$ compared to withdrawal

(51) Int. Cl.
*A61K 33/26* (2006.01)
*A61K 33/42* (2006.01)
*A61K 33/18* (2006.01)
*A61K 33/30* (2006.01)
*A61K 33/34* (2006.01)
*A61K 33/32* (2006.01)
*A61K 33/24* (2019.01)
*A61K 33/20* (2006.01)
*A61K 33/00* (2006.01)
*A61K 31/01* (2006.01)
*A61K 31/05* (2006.01)
*A61K 31/198* (2006.01)

T-test results of percent entries into the aversive white CPP chamber for the baseline, amphetamine withdrawal period and post 8 weeks of either nutritional supplement or normal rat chow.

*$p<0.05$ compared to baseline   **$p<0.05$ compared to withdrawal

T-test results of percent time spent in the aversive white CPP chamber for the baseline, amphetamine withdrawal period and post 8 weeks of either nutritional supplementation or normal rat chow

*p<0.05 compared to baseline

**p<0.05 compared to withdrawal

Comparisons of mean percent time in the white chamber for the 4 treatment groups during withdrawal and post-8 weeks (ANOVA)

*$p<0.05$ compared to both SAL-S and SAL-N

** $p<0.05$ compared to AMP-S withdrawal and AMP-N for both withdrawal and post normal chow Results of ANOVA – comparisons of mean percent entries into the white chamber for the 4 treatment groups

*p<0.05 compared to saline (SAL-S and SAL-N)

**p<0.05 compared to AMP-S during withdrawal, and to AMP-N during withdrawal and after 8 weeks normal chow

METHOD AND COMPOSITION FOR AMELIORATING DRUG SEEKING BEHAVIOR

BACKGROUND OF THE INVENTION

Field of the Invention

The present invention relates to methods and compositions for ameliorating drug-seeking behavior.

Description of the Background

Substance dependence and substance abuse, previously considered to be separate entities, have recently been incorporated into the disorder classified in the DSM-5 as Drug Addiction. The now recognized brain disease called drug addiction is a chronically relapsing disorder, characterized by compulsion to seek and take the drug, loss of control in limiting intake, and emergence of a negative emotional state (e.g., dysphoria, anxiety, irritability) when access to the drug is prevented. There are currently three recognized stages of drug addiction, namely i) the basal ganglia-driven binge/intoxication stage, ii) extended amygdala-driven withdrawal/negative affect stage, and iii) prefrontal cortex-driven preoccupation/anticipation stage. Each stage is associated with disturbances in a specific series of neural subsystems, and involves complex neurotransmitter interactions.

The ability of a drug of abuse to induce reward or intoxication is initially, although not solely related to its ability to increase levels of dopamine, particularly in the nucleus accumbens of the basal forebrain. This site-specific increase in dopamine then enables the individual to predict reward, imprint incentive value to reinforcers and rapidly learn reward associations. This means that the power to create an addiction does not merely lie in induction of timely hedonic pleasure, but in the evolution of complex neuroadaptations, involving dopamine and such other neurotransmitters and receptors as glutamate, GABA, endocannabinoid, and opioid. They synergistically produce the behaviors associated with addiction. Research on addiction trajectories has shown that the continued use of an abused substance gradually impairs neuronal function, eventually impacting the very capacity to exert free will.

Amphetamine is a powerful stimulant of the central nervous system with high addictive potential. It is also notably anorexogenic. The amphetamine-induced peptides, known as cocaine and amphetamine-regulated transcript (CART) 1 and 2, have been identified as being specifically produced upon administration of amphetamine to rodents. Via the brain, they exert anorexic effects and increase energy expenditure. CART is widely expressed in the central nervous system, including brain regions controlling food intake, and direct administration of CART decreases food intake. It is believed to increase metabolism by causing an increase in the release of thyrotropin-releasing hormone (TRH). The latter stimulates release of thyroid stimulating hormone, causing an increase in heat production by muscle and adipose tissue.

Amphetamine abusers therefore experience reduced food intake, increased caloric expenditure, and suffer from a malnutrition related to starvation. Starvation itself induces protein and fat catabolism that leads to loss of organ volume and function. Food restriction causing weight loss below approximately 15-20 percent of ideal body weight increases the potential for development of gastroparesis, with the associated nausea, early satiety and anorexia which may add to the nutritional insult of amphetamine abuse. Further, persons with gastroparesis are at high risk of developing small bowel bacterial overgrowth and the consequent increased gut transit, mal-digestion and malabsorption; painting a picture of an addict caught in a cycle of inadequate nutrition.

The gastrointestinal, neuronal and caloric perturbations resulting from amphetamine abuse are indicators that medical nutrition therapy is vital for individuals with substance use disorders. Disordered and dysfunctional eating patterns pervade attempts at abstinence, potentially worsening the withdrawal experience. Centers and caregivers are likely to have improved results if we address nutrition and abstinence simultaneously. Specific macro- and micronutrient supplementation treatment is recommended early in the treatment cycle, to supplement calories, neurotransmitter regulation and restoration of gut health.

SUMMARY OF THE INVENTION

Method: The Conditioned Place Preference (CPP) apparatus was used to test responses of amphetamine addicted rodents to oral administration of a nutritional supplement. Twenty-four male Sprague Dawley rats that previously showed the predicted baseline preference for the dark chamber during a 20-minute pre-test exploration of the CPP were selected. Twelve rats (Group AMP) were then given intraperitoneal injections of amphetamine hydrochloride and confined to the white (aversive) chamber, and their performance during a repeat exploration during acute withdrawal was compared with that of controls (Group SAL; n=12). Six rats in each of the addicted and control groups (Groups AMP-S and SAL-S) were then fed rat chow reconstituted with the nutritional supplement, while the remaining animals (Groups AMP-N and SAL-N) were fed normal rat chow for 8 weeks, followed by a final exploration, by all animals, of the CPP.

Results: After eight drug-free weeks of nutritional supplementation, previously amphetamine addicted animals (AMP-S) showed preference for the black CPP chamber, representing elimination of preference for the previously drug-paired chamber, measured as significantly fewer entries into, and significantly less time spent in the drug-paired white chamber ($p<0.05$). ANOVA revealed that addicted AMP-S rats behaved like non drug-exposed animals after 8 weeks of dietary supplementation.

Conclusion: Remarkable recovery from addictive behavior on the CPP paradigm was observed in established amphetamine addicts, after nutritional supplementation.

DETAILED DESCRIPTION

Figure 1:
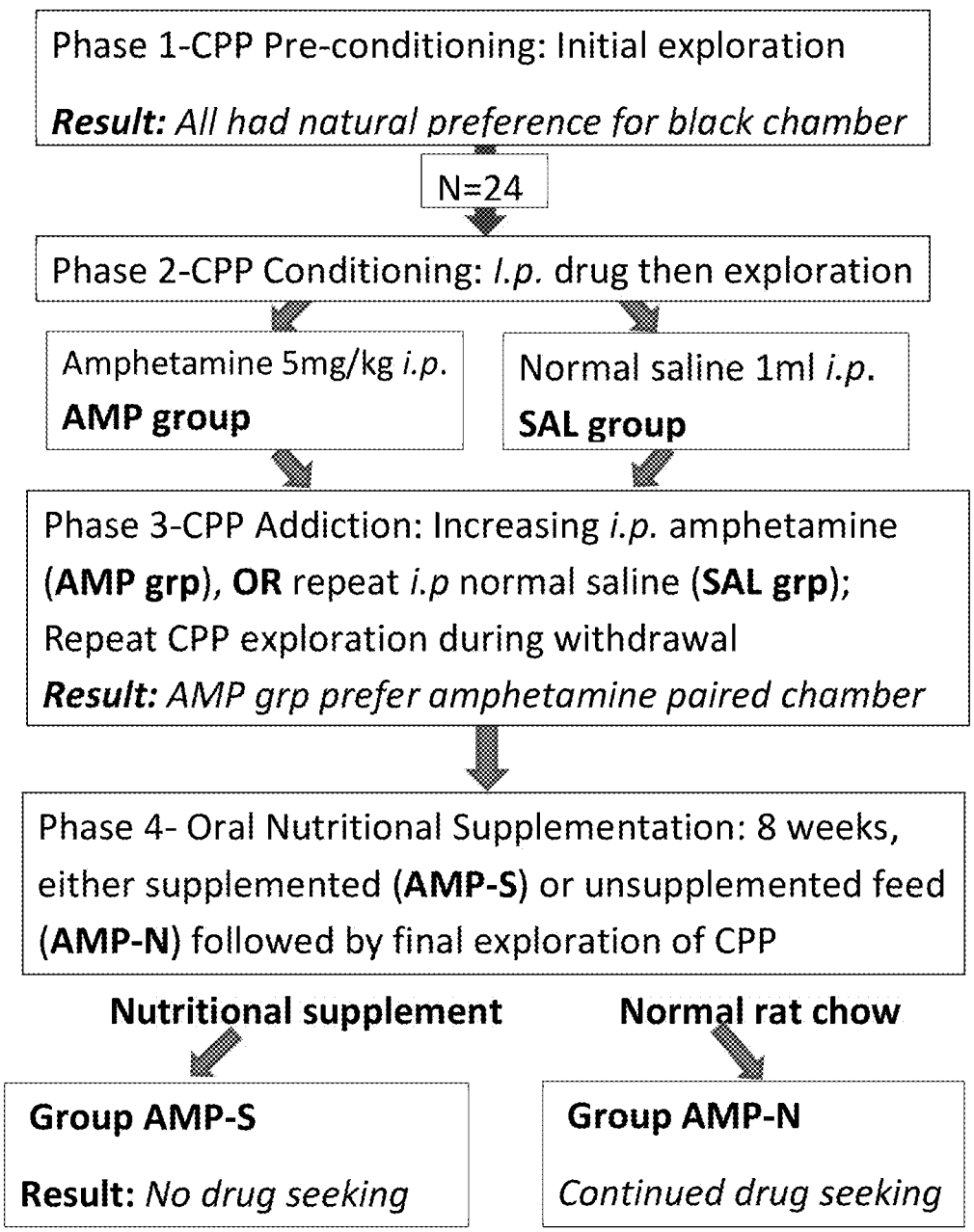
FIG. 1 is a representation of the experimental protocol that results in the present invention.

This experiment utilized the Conditioned Place Preference (CPP) Paradigm, the gold standard for rodent addiction studies, to create addiction, and test responses to nutritional supplementation.

A three (3) chambered CPP apparatus, measuring 75 cm×30 cm×25 cm, was employed. The single black, white and grey chambers could each be isolated from the other by a sliding door on either side of the central grey chamber. The box had a Perspex lid to facilitate viewing and video recording. The floor of the white chamber was covered with shiny transparent Perspex; while the floor of the black chamber was covered with wire mesh and sawdust, creating two contrasting chambers with distinct visual and tactile cues, representing a biased paradigm. The apparatus was thoroughly cleaned with a dilute solution of disinfectant upon completion of exploration by each rat.

Twenty four (24), three (3) month old male Sprague-Dawley rats, weighing approximately 250-350 g each, were obtained from the University of the West Indies Faculty of Medical Sciences Animal House following ethical approval of the protocol by the FMS/UHWI/UWI Ethics Committee, on the Mona Campus of the University of the West Indies. Animals were housed in pairs, in a normal twelve (12) hour light: dark cycle and fed food and water ad libitum.

Phase 1: Pre-conditioning, selection and first group assignments: Animals were selected for inclusion in the experiment via pre-conditioning. They were allowed an initial twenty (20) minute exploration of the CPP apparatus, and scores of chamber entries and time counted from a video recording. Animals displaying ≥80% preference for the dark CPP chamber during pre-conditioning were selected and randomly assigned to one of two treatment groups, AMP or SAL, each containing twelve animals.

Phase 2: Conditioning: During the conditioning phase, rats assigned to the amphetamine treatment group (Group AMP) received 1 ml of amphetamine hydrochloride (sigma) dissolved in 0.9% saline, providing 5 mg/kg intraperitoneally (i.p.). Rats in Group SAL were given 1 ml of physiological saline intraperitoneally.

Conditioning consisted of 8 days of daily, group-assigned intraperitoneal injection and then immediate, individual confinement to the white, 'aversive' chamber for thirty (30) minutes. On days 1, 3, 5 and 7, group AMP received white-paired amphetamine, while on the four alternate days (i.e., Day-2, 4, 6, 8), all of the animals received an injection of saline and were confined individually for 30 minutes to the black 'preferred' chamber. Therefore for group AMP, amphetamine was paired with the white chamber, while saline was paired with the black chamber (9,10). Control rats (Group SAL) were administered 1 ml 0.9% physiological saline on all eight days and individually confined for 30 minutes to the white chamber on days 1, 3, 5 and 7; and to the black chamber on days 2, 4, 6 and 8. The initial 8 days of i.p. treatments completed the conditioning phase of the experiment.

Phase 3: Amphetamine addiction and drug withdrawal: On day 9, the addiction phase ensued, with a six (6) day period of exposure to a daily increasing amphetamine dose for the drug treated (Group AMP) animals. Those rats were given six daily doses of 5, 5, 6, 6, 7 and 7 mg/kg/ml, i.p., respectively. Normal saline was repeatedly injected intraperitoneally to the rats in group SAL which provided controls for the addiction phase. Withdrawal followed the addiction phase. Rats then underwent three days without drug, saline or CPP exposure, and were fed regular rat chow with water ad libitum. On day 4 of withdrawal each animal was individually placed in the grey start chamber, enclosed by sliding doors, and then allowed a twenty (20) minute free exploration of the CPP box after the sliding doors were removed. During this period, the number of entries made into each chamber and the time spent in each chamber were recorded for all rats via scores from video recordings of exploration.

Phase 4: Oral nutritional supplementation: The orally administered, nutritional supplement used in this study contained the following:

| Ingredient | Dose | Range |
|---|---|---|
| L-Tyrosine | 1.6 g | 1.44-1.76 g |
| Amino-acid complex | 1.4 g | 1.26-1.64 g |
| Fish oil (DHA/EPA) | 2.2 g | 1.08-1.26 g |
| Vitamin B6 | 0.3 g | 0.23-0.28 g |
| Magnesium oxide | 0.1 g | 0.09-0.11 g |
| Calcium carbonate | 0.5 g | 0.18-0.22 g |
| Multi-vitamin tablet(s), including the following | | |
| Vitamin A | 4.1 mg | 3.8-4.6 mg |
| Vitamin C | 180 mg | 160-200 mg |
| Vitamin D3 | 0.02 mg | 0.018-0.022 mg |
| Vitamin E | 54 mg | 48.6-59.4 mg |
| Vitamin K | 0.05 mg | 0.045-0.055 mg |
| Thiamine | 3.0 mg | 2.7-3.3 mg |
| Riboflavin | 3.4 mg | 3.0-3.7 mg |
| Niacin | 40 mg | 18-22 mg |
| Vitamin B6 | 4 mg | 1.8-2.2 mg |
| Folic Acid | 1.0 mg | 0.9-1.1 mg |
| Vitamin B12 | 0.012 mg | 0.01-0.014 mg |
| Biotin | 0.06 mg | 0.054-0.066 mg |
| Pantothenic Acid | 20 mg | 18-22 mg |
| Calcium | 400 mg | 350-440 mg |
| Iron | 36 mg | 32-40 mg |
| Phosphorus | 0.22 mg | 0.20-0.24 mg |
| Iodine | 0.30 mg | 0.27-0.33 mg |
| Magnesium | 200 mg | 180-220 mg |
| Zinc | 22 mg | 20-24 mg |
| Selenium | 0.110 mg | 0.100-0.120 mg |
| Copper | 1.8 mg | 1.6-2.0 mg |
| Manganese | 4.6 mg | 4.1-5.0 mg |
| Chromium | .07 mg | 0.063-0.77 mg |
| Molybdenum | .09 mg | 0.081-.099 mg |
| Chloride | 144 mg | 130-158 mg |
| Potassium | 160 mg | 144-176 mg |
| Silica | 4.0 mg | 3.6-4.4 mg |
| Lycopene | 0.60 mg | 0.54-0.66 mg |
| Lutein | 0.50 mg | 0.45-0.55 mg |
| Boron | 0.30 mg | 0.27-0.33 mg |
| Tin | 0.020 mg | 0.018-0.022 mg |
| Vanadium | 0.020 mg | 0.018-0.022 mg |
| Nickel | 0.010 mg | 0.009-0.011 mg |

Nutritionally supplemented animals were proportionally fed a combination of the named components, at 0.123 g/day, 0.123 g/day and 0.0408 g/day, respectively, for eight weeks. These doses were for a 350 g rat, Preparation of the supplement for oral treatment involved crushing and weighing the megavitamins, whereas the fish oil tablets were opened and drained into a calibrated beaker and the relevant volumes removed. Supplement capsules were also opened and the powder weighed for correct dosing. All animals were individually caged for the duration of the supplementation period.

The initial Groups AMP and SAL were further divided and randomly assigned to either supplementation or normal rat chow, as indicated below:

Group AMP-S: Amphetamine treated rats, to be fed with supplement after addiction phase
  Group AMP-N: Amphetamine treated rats, to be fed with normal rat chow throughout the experiment Group SAL-S: Saline treated rats, to be fed with supplement after addiction phase Group SAL-N: Saline treated rats, to be fed with normal rat chow throughout the experiment Members of the supplemented groups (i.e., groups AMP-S and SAL-S) received supplemented chow as first feed daily for the 8-week treatment period. Non-supplemented, standard rat chow was administered for the rest of the day, only after chow with supplement was fully consumed. The non-supplemented groups (i.e., groups AMP-N and SAL-N) were administered food and water ad libitum throughout the day. Those eight weeks were followed by a final 20-minute exploration of the CPP by all rats.

All the resulting data were analyzed, using the SPSS 19 software. The mean percent time and entries into the white CPP chamber by each animal were scored from video recordings. Pre-drug, withdrawal and post-8 week mean scores for white chamber entries and time were analyzed within groups using the t-test. Comparisons of the mean percent time and entries into the white CPP chamber were also measured between groups, and analyzed using one-way ANOVA. Post-hoc analysis was performed via the Tukey test due to the nature of the group means.

Pre-Conditioning

A robust pre-conditioning milieu was created before drug treatment was initiated. Rats in all 4 treatment groups had significantly higher baseline percent entries into and time in the black chamber (p<0.05) prior to test conditions.

Figure 2:
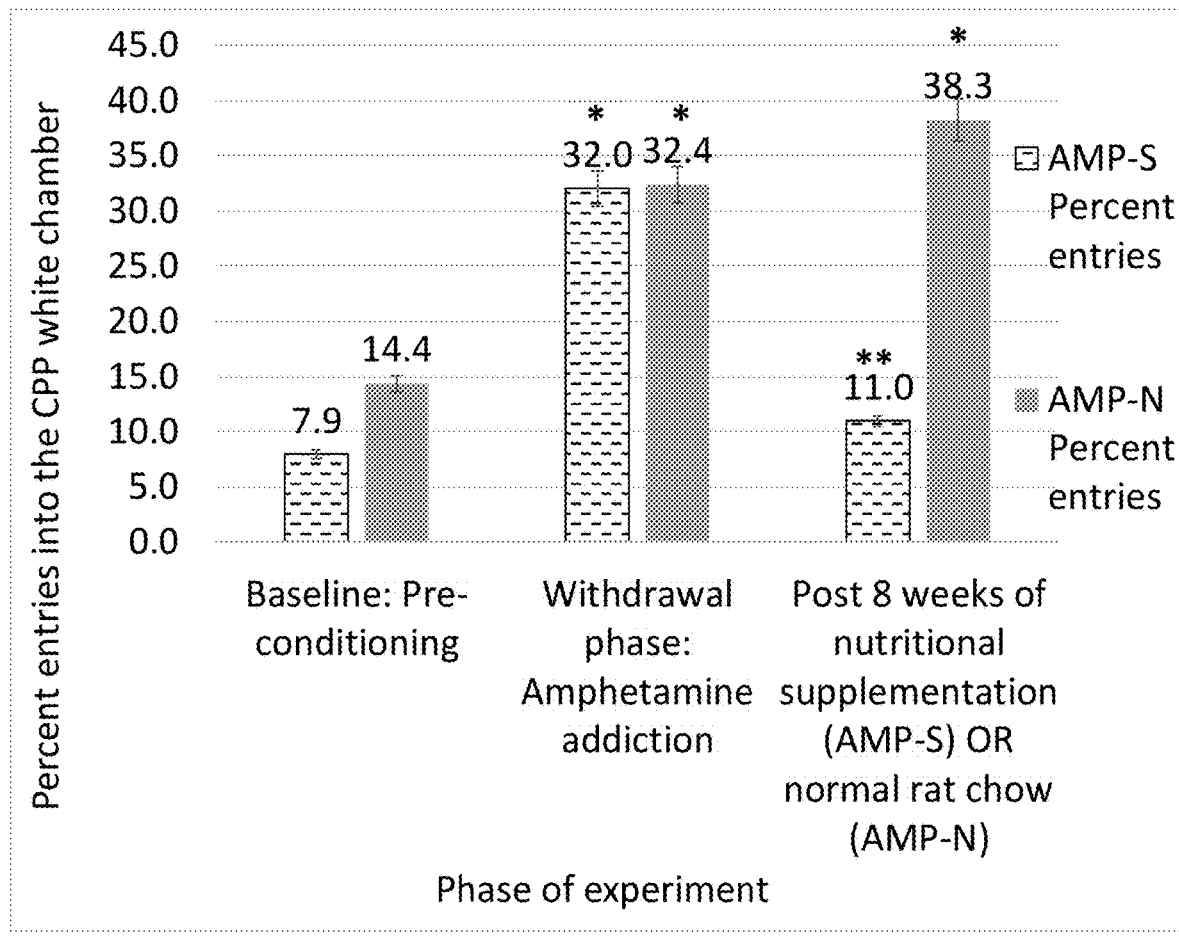
FIG. 2 is a chart showing the percent entries of amphetamine-addicted rats in different experimental groups into the CPP chamber at various stages in the experiment.

Comparison of Mean Percent Entries into the White CPP Chamber for Groups AMP-S and AMP-N: Results of t Test (FIG. 2)

Amphetamine-treated rats in both groups AMP-S and AMP-N made significantly more entries into the drug-paired white chamber of the CPP during withdrawal, compared to their performance during pre-conditioning (p<0.001).

After eight (8) weeks of consuming the nutritional supplement there was a significant decrease in entries into the drug-paired chamber (p<0.05) by rats in group AMP-S. Also, there was no significant difference between the initial pre-conditioning entries and those noted after 8 weeks of supplementation. On the other hand rats in group AMP-N continued to make significantly more entries into the white chamber after 8 weeks of standard rat chow.

Figure 3:
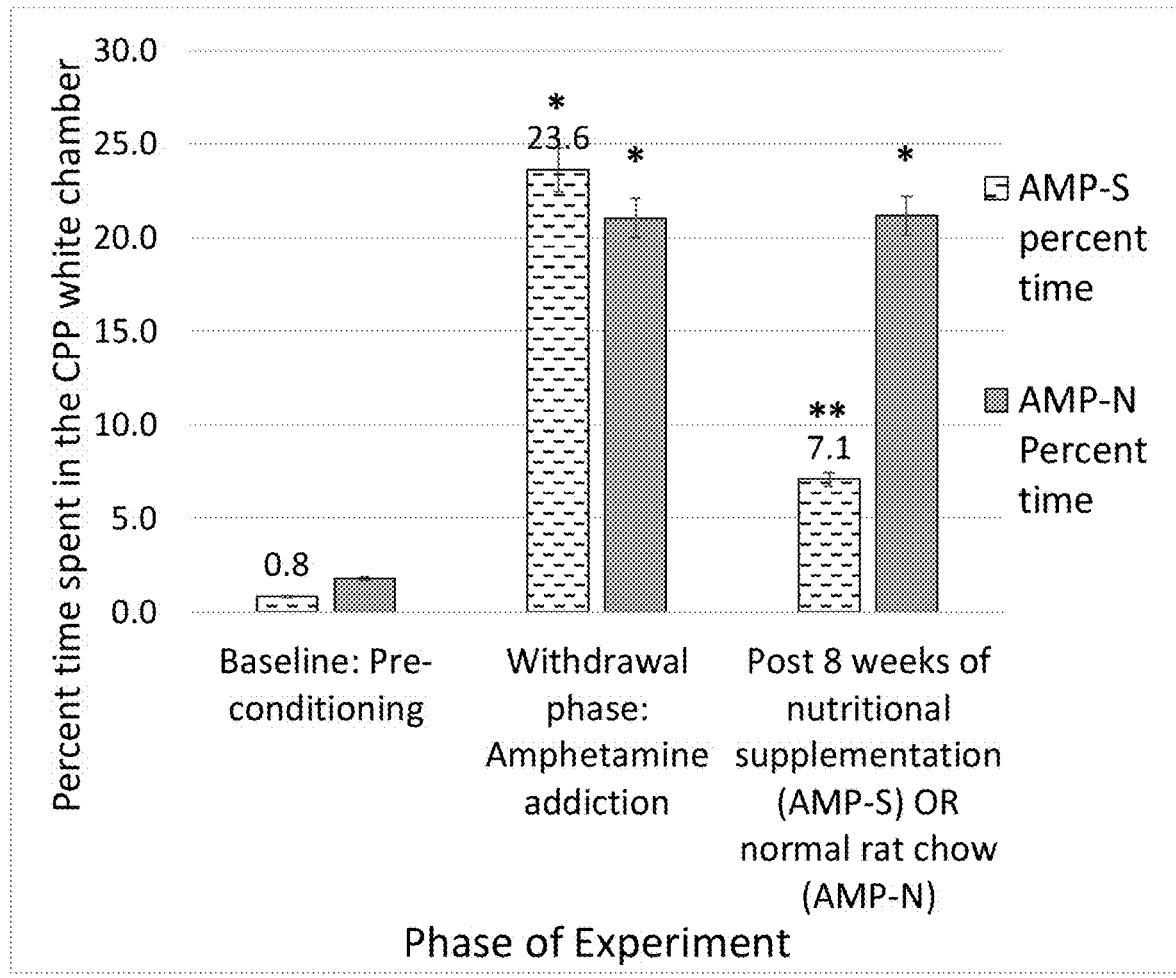
FIG. 3 is a chart showing the percent time spent by amphetamine-addicted rats in different experimental groups in the CPP chamber at various stages in the experiment.

Comparison of Mean Percent Time in the White CPP Chamber for Groups AMP-S and AMP N: Results of t Test (FIG. 3)

Amphetamine-treated rats in both groups AMP-S and AMP-N spent significantly more time in the drug-paired white chamber of the CPP during withdrawal, compared to their performance during pre-conditioning (p<0.001).

After eight (8) weeks of consuming the nutritional supplement there was a significant decrease time spent in the drug-paired chamber (p<0.05) by rats in group AMP-S. Also, there was no significant difference between the initial pre-conditioning white chamber time, and those noted after 8 weeks of supplementation.

Figure 4:
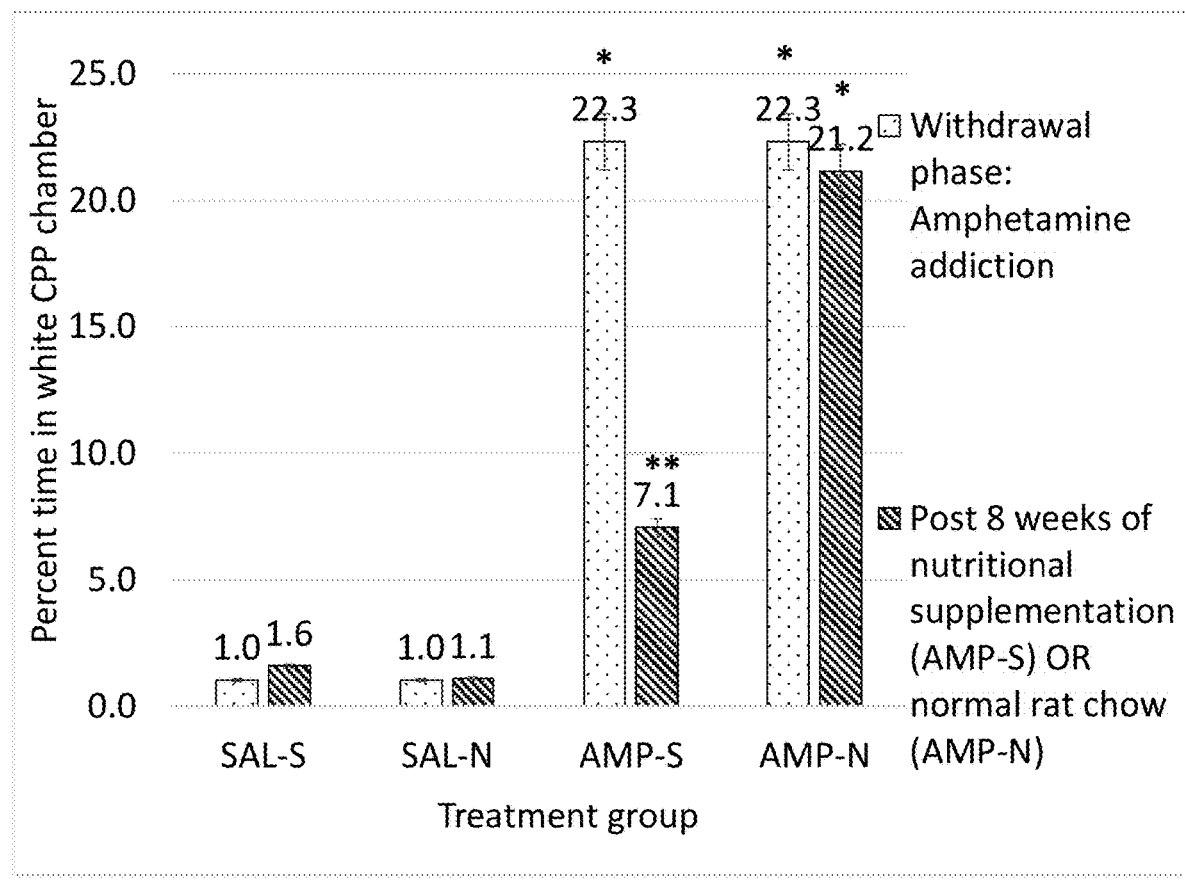
FIG. 4 is a chart showing the percent time spent by all experimental groups of rats in the CPP chamber during the withdrawal phase and post 8 weeks.

Comparison of Mean Percent Time in White, Drug-Paired Arm for all Phases of the Experiment (FIG. 4)

During withdrawal, amphetamine treated rats (Groups AMP-S and AMP-N, the means of which are combined n=12) showed a significantly increased percent time spent in the drug-paired white chamber, compared to the saline treated groups (SAL-S and SAL-N combined n=12) (p<0.01).

After 8 weeks of Nutritional supplementation, previously amphetamine addicted rats in Group AMP-S spent significantly less time in the previously drug-paired white chamber, compared to both saline treated groups, SAL-S and SAL-N. After 8 weeks of standard, non-supplemented chow, amphetamine-addicted rats in Group AMP-N continued to spend significantly more time in the drug paired white chamber (p<0.01) compared to saline treated groups, SAL-S and SAL-N.

Figure 5:
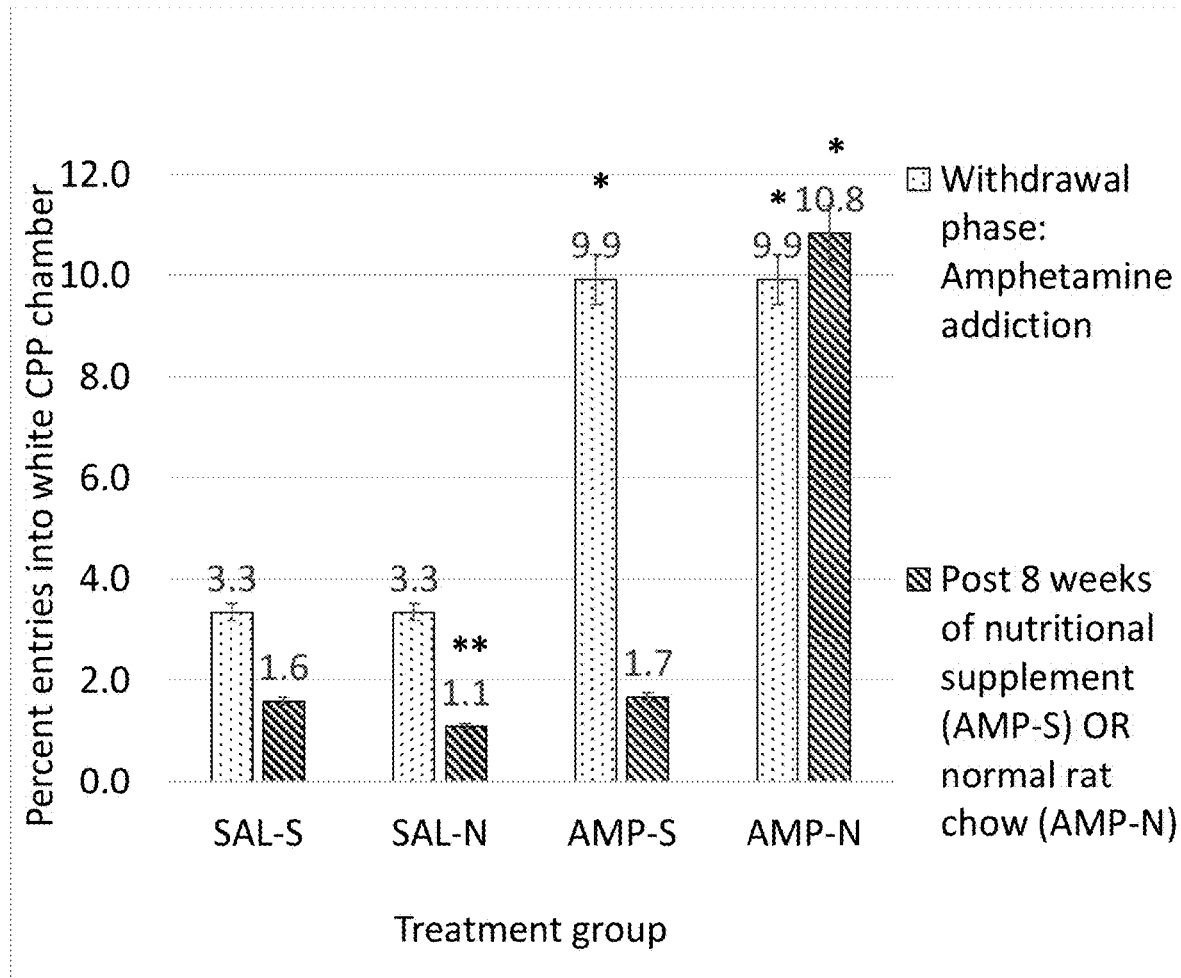
FIG. 5 is a chart showing the percent entries spent by all experimental groups of rats in the CPP chamber during the withdrawal phase and post 8 weeks.

Comparison of Mean Percent Entries into White Arm of CPP for all Groups (FIG. 5)

After drug dosing, during the withdrawal period, amphetamine treated rats (Groups AMP-S and AMP-N; n=6 each) made significantly higher percent entries into the drug-paired white chamber, compared to the saline treated groups (SAL-S and SAL-N; n=6 (p<0.01).

After 8 weeks of Nutritional supplementation, previously amphetamine addicted rats in Group AMP-S made significantly fewer entries into the previously drug-paired white chamber, compared to both saline treated groups, SAL-S and SAL-N.

After 8 weeks of standard, non-supplemented chow, amphetamine-addicted rats in Group AMP-N continued to make significantly more entries into the previously drug paired white chamber (p<0.01) compared to saline treated groups, SAL-S and SAL-N.

Summary of Main Findings

For the first time, complete reversal of drug seeking in stimulant-addicted animals has been demonstrated, after application of a solely nutritional intervention.

The widely accepted criteria of acquisition of addiction using the Conditioned Place Preference paradigm were evident in our baseline results. At baseline, all of the animals spent significantly less time in the white chamber, than they did in the black, naturally preferred chamber. Amphetamine administration paired with the white CPP chamber significantly increased the percent entries into, and percent time spent in the otherwise aversive white chamber during withdrawal (p<0.05). Then, eight weeks of rat chow re-constituted to incorporate the nutritional supplement resulted in the behavioral transition to significantly fewer entries into, and time spent in the white chamber (p<0.05). Amphetamine addicts were found to be no different in white chamber time and entries than the saline-treated animals. The saline treated controls maintained 'baseline' white chamber aversion throughout the experiment.

The results of this study have the potential to profoundly revolutionize therapeutic management of drug addiction. The nutritional supplement disclosed herein has been shown to influence and reduce drug seeking by amphetamine addicts on the most utilized and trusted animal model of drug addiction, the Conditioned Place Preference paradigm.

The invention claimed is:

1. A method for ameliorating drug-seeking behavior in drug addicts who have stopped using the addicted-to drug and who have reestablished non-addict physiological chemical balance, comprising administering to the drug addicts a therapeutically effective amount of a nutritional supplement comprising the following:

| Ingredient | Range (g)** |
|---|---|
| L-Tyrosine | 1.44-1.76 g |
| Amino-acid complex | 1.26-1.64 g |
| Fish oil (DHA/EPA) | 1.08-1.26 g |
| Vitamin B6 | 0.23-0.28 g |
| Magnesium oxide | 0.09-0.11 g |
| Calcium carbonate | 0.18-0.22 g |
| Multi-vitamin tablet(s), including the following | |

-continued

| Ingredient | Range (g)** |
|---|---|
| Vitamin A | 3.8-4.6 mg |
| Vitamin C | 160-200 mg |
| Vitamin D | 0.018-0.022 mg |
| Vitamin E | 48.6-59.4 mg |
| Vitamin K | 0.045-0.055 mg |
| Thiamine | 2.7-3.3 mg |
| Riboflavin | 3.0-3.7 mg |
| Niacin | 18-22 mg |
| Vitamin B6 | 1.8-2.2 mg |
| Folic Acid | 0.9-1.1 mg |
| Vitamin B12 | 0.01-0.014 mg |
| Biotin | 0.054-0.066 mg |
| Pantothenic Acid | 18-22 mg. |

2. The method of claim 1, wherein the nutritional supplement comprises the ingredients in the following amounts:

| Ingredient | Dose (g)* |
|---|---|
| L-Tyrosine | 1.6 g |
| Amino-acid complex | 1.4 g |
| Fish oil (DHA/EPA) | 2.2 g |
| Vitamin B6 | 0.3 g |
| Magnesium oxide | 0.1 g |
| Calcium carbonate | 0.5 g |
| Vitamin A | 4.1 mg |
| Vitamin C | 180 mg |
| Vitamin D3 | 0.02 mg |
| Vitamin E | 54 mg |
| Vitamin K | 0.05 mg |
| Thiamine | 3.0 mg |
| Riboflavin | 3.4 mg |

-continued

| Ingredient | Dose (g)* |
|---|---|
| Niacin | 40 mg |
| Vitamin B6 | 4 mg |
| Folic Acid | 1.0 mg |
| Vitamin B12 | 0.012 mg |
| Biotin | 0.06 mg |
| Pantothenic Acid | 20 mg. |

3. The method of claim 1, wherein the nutritional supplement further comprises:

| Ingredient | Dose |
|---|---|
| Calcium | 400 mg |
| Iron | 36 mg |
| Phosphorus | 0.22 mg |
| Iodine | 0.30 mg |
| Magnesium | 200 mg |
| Zinc | 22 mg |
| Selenium | 0.110 mg |
| Copper | 1.8 mg |
| Manganese | 4.6 mg |
| Chromium | .07 mg |
| Molybdenum | .09 mg |
| Chloride | 144 mg |
| Potassium | 160 mg |
| Silica | 4.0 mg |
| Lycopene | 0.60 mg |
| Lutein | 0.50 mg |
| Boron | 0.30 mg |
| Tin | 0.020 mg |
| Vanadium | 0.020 mg |
| Nickel | 0.010 mg. |

* * * * *